United States Patent

Karpf et al.

[11] Patent Number: 5,128,019
[45] Date of Patent: Jul. 7, 1992

[54] DEVICE FOR MEASURING CHEMICAL AND PHYSICAL PARAMETERS OF A LIQUID OR GASEOUS MEDIUM

[75] Inventors: Hellfried Karpf; Helmut Offenbacher; Erich Kleinhappl, all of Graz; Hermann Marsoner, Steinberg; Ewald Jöbstl, Graz, all of Austria

[73] Assignee: AVL Medical Instruments AG, Schaffhausen, Switzerland

[21] Appl. No.: 437,202

[22] Filed: Nov. 16, 1989

[30] Foreign Application Priority Data

Dec. 1, 1988 [AT] Austria .................. 2958/88

[51] Int. Cl.$^5$ .................................. G01N 27/26
[52] U.S. Cl. .................... 204/416; 204/418; 204/419; 422/82.06; 422/82.07; 356/317; 356/318
[58] Field of Search .......... 204/416, 418, 419; 356/317, 318; 250/458.1, 459.1; 422/82.06, 82.07

[56] References Cited

U.S. PATENT DOCUMENTS

| | | | |
|---|---|---|---|
| 4,003,707 | 1/1977 | Lubbers | 128/634 |
| 4,306,877 | 12/1981 | Lubbers | 204/415 |
| 4,892,640 | 1/1990 | Wolfbeis et al. | 204/416 |
| 5,017,339 | 5/1991 | Marsoner et al. | 204/411 |

Primary Examiner—John Niebling
Assistant Examiner—Bruce Bell
Attorney, Agent, or Firm—Watson, Cole, Grindle & Watson

[57] ABSTRACT

In order to reduce the measuring volume in a device for measuring chemical and physical parameters of liquid or gaseous media by means of optical sensor elements whose optodes may be replaced easily, a measuring unit with a sample channel is provided which may be inserted into a supporting frame of the device and which may be connected to ingoing and outgoing sample lines via capillary bores. The measuring unit contains a sensor carrier forming the boundary of the sample channel on one side, which sensor carrier has bores holding the optodes. The indicator film of each individual optode is situated in the plane of the sensor carrier facing the sample channel.

20 Claims, 4 Drawing Sheets

DEVICE FOR MEASURING CHEMICAL AND PHYSICAL PARAMETERS OF A LIQUID OR GASEOUS MEDIUM

BACKGROUND OF THE INVENTION

This invention relates to a device for measuring chemical and physical parameters of a liquid or gaseous medium, comprising at least one optical sensor element (optode) in contact with the medium, and units for optical excitation of the indicator film of the optode and for detection and evaluation of the optical signals determined by the parameters to be measured.

DESCRIPTION OF THE PRIOR ART

Optical sensor elements, i.e., so-called optodes, have been known for some time now and are becoming increasingly popular in many areas, above all in medical analysis and in the field of biotechnology.

In EP-A-0 109 959, for example, a sensor element for determining the $O_2$ content of a sample is described, whose bottom layer connected to an illuminating and light measuring device is configured as a glass substrate. The middle layer is a polymer film containing the fluorescent indicator in molecular distribution in such a way that a fluorescence signal depending on the oxygen content of the sample material can be measured. On top of the polymer film there is an optical insulating layer adjacent to the sample material. The polymer film and the insulating layer are homogeneously bonded by polymerization, and are made of a polymer material with good oxygen permeability. The polymer film, preferably of a cured silicone polymer, contains the indicator in solubilized form. Preferred indicators are polycyclic, homocyclic or heterocyclic aromatic molecules, for instance polycyclic aromatic hydrocarbons with fluorescence decay times greater than 5 ns. A corresponding device for practical use of such an optode in the laboratory will not be discussed herein, however.

A measuring device for determining the $CO_2$ content of a sample is described in EP-A-105 870, comprising a pH-dependent fluorescent dye as an indicator, which is embedded in aqueous solution in a proton-impermeable, gas-permeable polymer membrane. In this instance the aqueous indicator solution is embedded in the polymer film, e.g., in silicone rubber, in the form of droplets of a size of 0.1 to 100 micrometers, which are provided in homogeneous distribution. The polymer membrane incorporating the indicator droplets (micellae) is moulded or grafted onto the smooth surface of a transparent supporting element.

Finally, a pH sensor is described in (4A 1833/87), whose sensitive layer is covered by a hydrophilic, ion-permeable polymer membrane, e.g., made or regenerated cellulose. In order to suppress stray light, this polymer membrane contains pigments of a precious metal precipitated by a reduction or reduction/cementation technique. Due to the poor adhesive propoties of the polymer membrane, it is fastened mechanically, for instance by clamps. As before, it is only the sensor itself and its fabrication as well as the principle of measurement that are described in this publication, whereas a practicable measuring device with optical sensors of the above type is not disclosed there.

SUMMARY OF THE INVENTION

Based on the above state of the art the invention is concerned with proposing a measuring device with one or more optical sensor elements, which is characterized by a minimum measuring volume and a simplicity of design permitting easy replacement of the optical sensor elements, the optical contacts with the sensor elements and the gastight contact with the sample medium being established in a simple way.

In the invention this object is achieved by providing a unit for insertion into a supporting frame of the device, which unit comprises a measuring chamber and a sample channel, the latter being connected via capillary bores to ingoing and outgoing sample lines, and by further providing that this measuring unit also comprises a sensor carrier forming the wall of the sample channel on one side and having bores holding the optodes, and that the indicator film of each individual optode is situated in the plane of the sensor carrier facing the sample channel. Preferably, the entire unit comprising the measuring chamber and the sample channel and the optodes located in the sensor carrier should be replaceable as a whole. After this unit has been inserted into the supporting frame of the device, it is centered and connected via capillary bores to the ingoing and outgoing sample lines of the analyzing apparatus. In this manner it is easy to replace individual sensor elements when they have been contaminated or reached the end of their useful life.

In order to simplify optical coupling of the measuring unit, it is proposed in a further development of the invention that the individual optodes be provided with optically transparent carrier elements located in the bores of the sensor carrier, which elements end level with the plane of the sensor carrier facing away from the sample channel, and that an optical fiber connector be provided, which should have optical connections for each optode, i.e., preferably two-armed lightguides, the ends of these lightguides being situated in a surface-polished plate that may be put into contact with the sensor carrier.

In a particularly convenient variant of the invention the supporting frame of the device is furnished with a spring-loaded coupling element in connection with the outgoing sample line, which will center the measuring unit and press it against a coupling element connected with the ingoing sample line, sealing elements being arranged between the coupling elements and the capillary bores connected with the sample channel, and the spring-loaded coupling element having a press lever releasing it. The device operates as follows. The measuring unit is inserted vertically into the corresponding opening in the supporting frame, and is locked in place by a slight pressure against the coupling elements. During this process the spring-loaded coupling element will give way against the force of the spring until a centering nose of the coupling element facing the measuring unit engages a particular recess of this unit. The measuring unit is removed by pressing a lever of the supporting frame, such that the spring-loaded coupling element is again shifted against the force of the spring until the centering nose of the coupling element will disengage from its special recess and subsequently release the measuring unit.

The tight connection between the capillary bores of the measuring unit and the rest of the sample path is due to the coupling elements being pressed by the spring against the corresponding bores in the measuring unit, which bores are packed with sealing elements, i.e., preferably sealing rings.

The sensor carrier should be characterized by high chemical resistance to all kinds of sample constituents; besides, it should permit bores for the individual optodes with the smallest possible tolerances, and it should have good heat conducting properties. For these reasons the invention proposes that the sensor carrier be configured as a corrosion-resistant metal disk, preferably of anodized aluminium, in which the bores for the optodes are placed along the diameter of the metal disk, and the optodes, preferably for measuring pH- and $pO_2$- and $pCO_2$-values, are sealed into these bores.

In order to facilitate the process of sealing the optodes into the sensor carrier, and, above all, to prevent the sealant from seeping onto the surface of the sensor carrier next to the sample, it is proposed that a capillary gap be formed between the individual optodes and the bores in the sensor carrier, which should be packed with sealant, and that the sealant should be filled into one or more groove-shaped recesses at the periphery of each bore, extending almost as far as to the plane of the sensor carrier adjacent to the sample channel.

The pH-optode of the invention is covered by a sleeve containing the optically-transparent carrier element and carrying in a circumferential groove a flexible fastening element for a protein-impermeable membrane covering the active area of the pH-optode, preferably made of regenerated cellulose, the capillary gap in the sensor carrier situated between sleeve and bore being packed with sealant. In order to avoid sealing problems with the swelling, protein-impermeable membrane of the pH-optode, the optically transparent carrier elements is provided with a sleeve which will flexibly fasten the membrane in a circumferential groove, preferably by means of an O-ring.

In a preferred variant of the invention the sleeve is made of a plastics material, preferably one with a memory effect, which is shrunk onto the optically transparent carrier element.

In order to enhance the useful signal the proposal is put forward that the side-wall of the sleeve facing the carrier element be covered with a thin film whose refractive index is smaller than that of the carrier element.

It is of importance for all analyses that the sample in the sample channel should be free from bubbles. It should further be possible to check contamination of the sensors and the filling level of the sample channel. This is ensured in an enhanced variant of the invention, in which the measuring unit is made of optically transparent material, preferably plexiglass, and in which an optical waveguide is provided in the supporting frame of the measuring unit for the purpose of illuminating the sample channel. Via an external lighting source light of any wavelength may be introduced into the transparent measuring unit, the difference in the refractive indices of the sample, the walls of the sample channel and any contaminations or air bubbles permitting excellent optical monitoring.

Another advantage of the device according to the invention is that the optical fiber connector is provided with at least one heating element and one thermoelement for thermostat control of the sensor carrier in contact with the fiber connector.

For optical coupling of the measuring unit, it is further provided that the fiber connector should comprise a sleeve contained in a housing, which should hold the individual fibers and whose front end should carry the surface-polished plate which may be brought into contact with the sensor carrier, the waveguide sleeve being pressed against the sensor carrier at constant pressure, i.e., by the force of a spring supported by the housing. This will ensure firm but gentle optical and thermal coupling between the front end of the waveguide sleeve and the sensor carrier.

Advantages in mass-production of the measuring unit, as well as a reduction of the sample volume required for measurement, are obtained in the invention by configuring the sample channel in the measuring unit as a capillary groove extending over the entire indicator film of each individual optode, and by placing the capillary bores opening into the sample channel outside of the plane of the capillary groove, connecting them to the latter by short bores. This is particularly advantageous if the sensor carrier is sealed into the measuring unit, since the special arrangement of the capillary bores will prevent them from being blocked by the sealant.

In order to ensure good sample flow and to fill the capillary groove uniformly and completely, it is provided that the inlet opening angle $\alpha$ in the plane of the capillary groove should be 10° to 60°, preferably 15° to 25°, and that the outlet opening angle $\beta$ should be 10° to 90°, preferably 30° to 60°. The sample volume may be further reduced if the width of the capillary groove is reduced between the individual optodes, as is proposed in another variant of the invention.

By arranging for an asymmetric flow past the individual optodes the sample flow may be further improved in a device according to the invention.

BRIEF DESCRIPTION OF THE DRAWINGS

Following is a more detailed description of the invention as illustrated by the accompanying drawings, in which.

DETAILED DESCRIPTION OF THE PREFERRED EMBODIMENT

Figure 1:
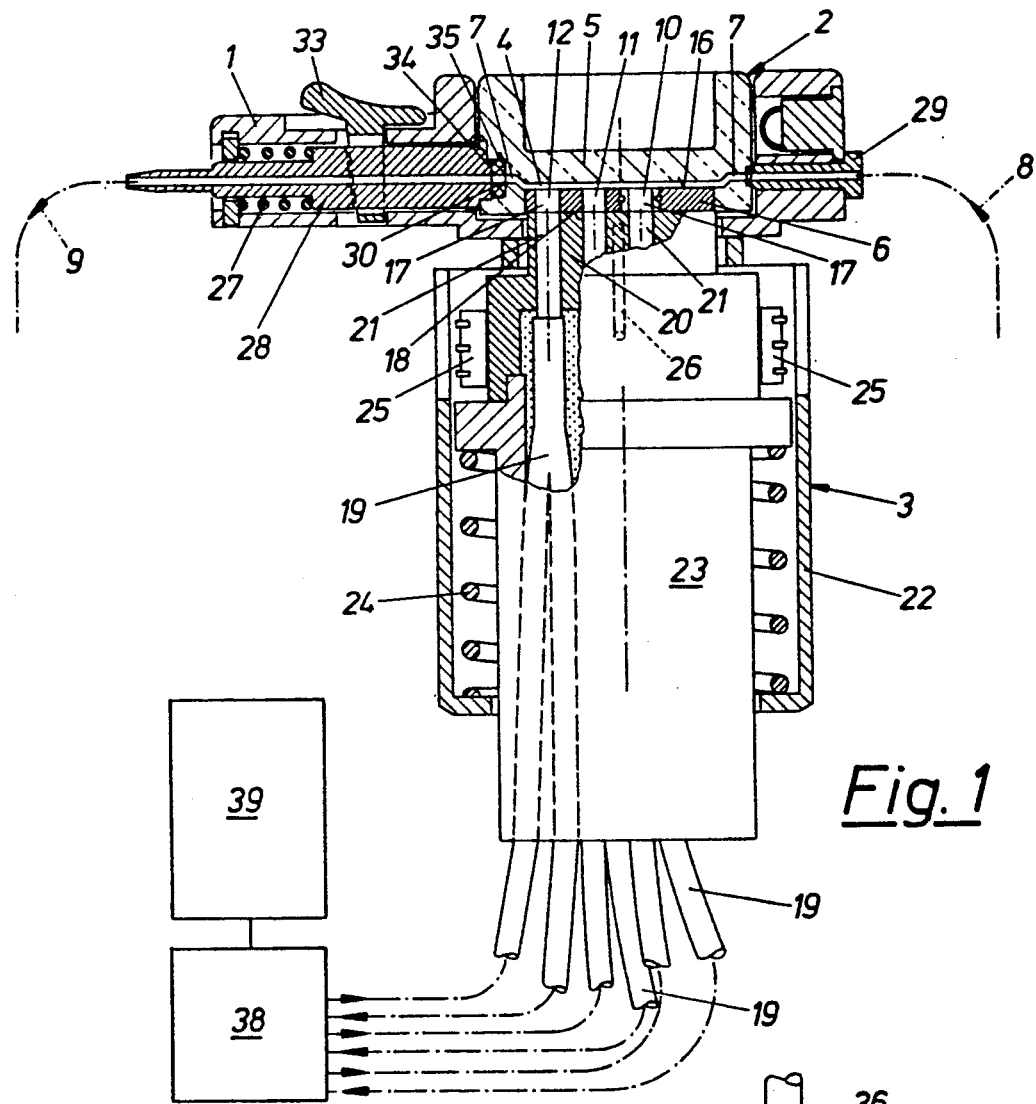
FIG. 1 shows a device according to the invention, as a section along line I—I in FIG. 2.
Figure 2:
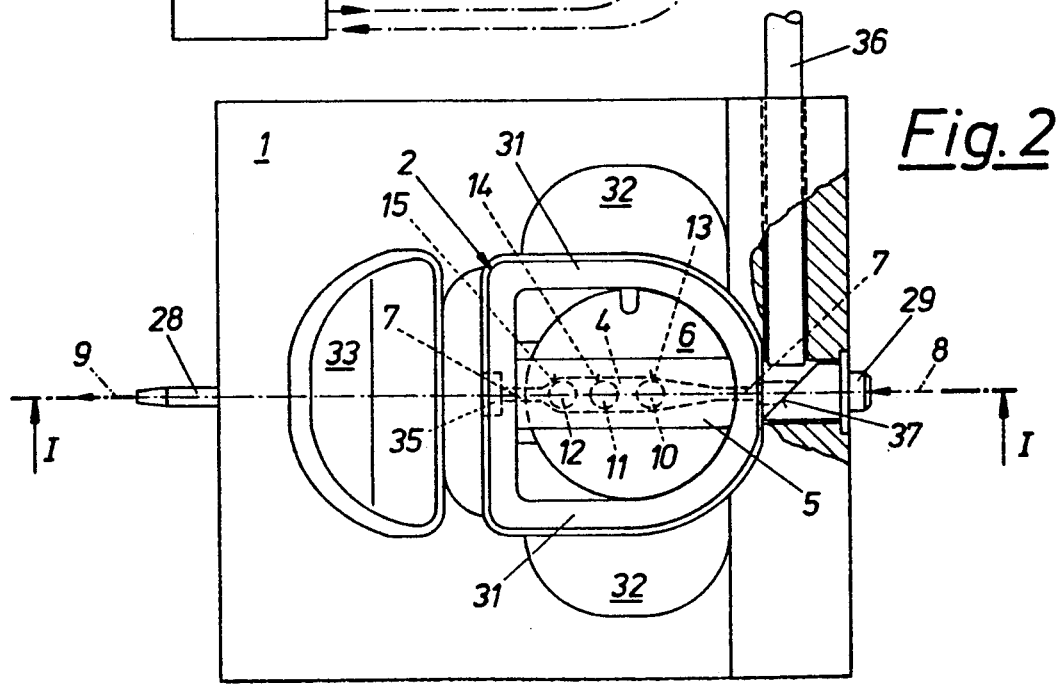
FIG. 2 is a view from above of the part as shown in FIG. 1.

The measuring device presented schematically in FIGS. 1 and 2 essentially comprises a supporting frame 1 into which is inserted the measuring unit 2, and an optical fiber connector 3 for optical communication with the measuring unit 2.

The sample channel 4 configured as a capillary groove is defined by a bridge 5 of the measuring unit 2 on one side and by a disk-shaped sensor carrier 6 on the other side, and is connected via capillary bores 7 to the ingoing sample line 8 and the outgoing sample line 9. The individual optodes 10, 11, 12 are sealed into corresponding bores 13, 14, 15 of the sensor carrier in such a way that the indicator film, or rather the active area of each optode lies in the plane 16 of the sensor carrier 6 facing the sample channel 4.

Figure 3:
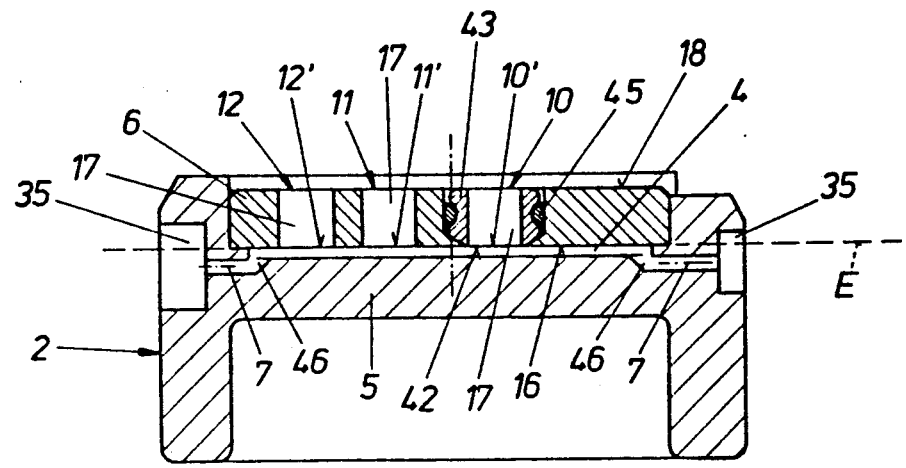
FIG. 3 presents a detail of a measuring unit of the device of FIG. 1, as a section along line III—III in FIG. 4.

Each of the individual optodes 10, 11, 12 has an optically-transparent carrier element 17, which ends level with the plane 18 of the sensor carrier 6 facing away from the sample channel 4 (also see FIG. 3). The optical fiber connector 3 carrying a two-armed lightguide 19 for each optode is in contact with the plane 18 of the sensor carrier facing away from the sample, i.e., via a surface-polished plate 20 made from corrosion-resistant material, each of the statistically mixed joint ends 21 of the two-armed lightguides being assigned to one of the optically-transparent carrier elements 17 of optodes 10, 11, 12, the axes of both parts being parallel.

A fiber sleeve 23 of the optical fiber connector 3, which is located in a housing 22 attached to the frame 1 and contains the individual two-armed lightguides 19 potted in a sealant, is pressed, together with the front-side plate 20, against the sensor carrier 6 at constant pressure, i.e., by the force of a spring 24 supported by the housing 22. Precise thermostat control of the device is ensured by providing the optical fiber connector 3 with two heating elements 25 and a centrally arranged thermoelement 26, the electric supply lines and signal leads of which are not shown here in detail.

The frame 1 has a movable coupling element 28 loaded by a spring 27, which is connected with the outgoing sample line 9 and is used for centering and pressing the measuring unit 2 against a coupling 29 connected with the ingoing sample line 8, once the unit 2 has been inserted into the frame 1. Between the coupling elements 28, 29 and the capillary bores 7 opening into the sample channel 4 are located sealing elements 30, e.g., O-rings, which are placed in bores of the measuring unit 2.

As is seen in FIG. 2, recesses 32 are provided on either side of the manipulated part 31 of the measuring unit 2, which will facilitate handling during replacement of the measuring unit. The spring-loaded coupling element 28 may be moved away from the measuring unit 2 by actuating a press lever 33, such that the centering nose 34 of the coupling element 28 engaging the bore 35 for the sealing element 30 will release the measuring unit 2, which may then be removed.

For illumination of the sample channel 4 or the entire measuring unit 2 made of optically transparent material, a lightguide 36 is provided in the frame 1, which will supply light from a source (not shown here) via a mirror 37.

FIG. 1 also indicates units 38, 39 for optically exciting the indicator films of the individual optodes and for detecting and evaluating the optical signals.

Figure 4:
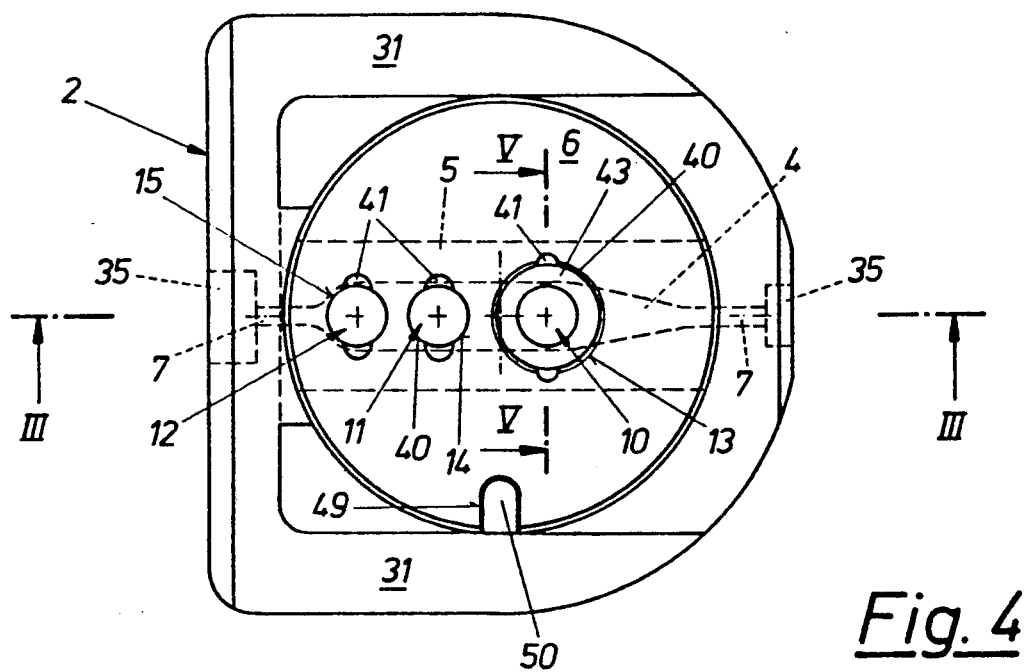
FIG. 4 is a view from above of the part as shown in FIG. 3, FIG. 5 gives a detail from FIG. 3, FIG. 6 gives a view from above of the optical fiber connector of the device as in FIG. 1, and FIGS. 7-9 give different variants of the sample channel of a measuring unit as in FIG. 3.

FIGS. 3 and 4 present a detail of the measuring unit 2 with the sealed-in sensor carrier 6. The sample channel 4 basically is configured as a capillary groove, which extends over the entire area of the indicator films 10', 11', 12' of the optodes 10, 11, 12 and which has a special shape to be described in detail below, which will favor sample flow. The capillary bores 7 opening into the sample channel 4 are situated outside of the plane E of the capillary groove to which they are connected by bores 46, as is seen in FIG. 3. This arrangement will prevent the ingoing lines from being blocked by sealant when the sensor carrier 6 is sealed into the measuring unit 2.

Suitable interlocking elements, such as a groove 49 in the sensor carrier 6 and a correspondingly formed projection 50 on the manipulated part 31 of the measuring unit, will facilitate precise alignment of the individual optodes relative to the sample channel 4.

Between the optically transparent carrier elements 17 of the individual optodes and the walls of the bores 13, 14, 15 there are capillary gaps 40, into which the sealant is entered through groove-shaped recesses 41 on the periphery of each bore 13, 14, 15 extending almost as far as to the plane 16 of the sensor carrier 6 adjacent to the sample channel. The capillary forces that are only active in the capillary gap 40 will keep the sealant from leaking at the boundary planes 16 and 18 of the sensor carrier, and the indicator films 10', 11', 12' of the individual optodes will be prevented from being contaminated.

The protein-impermeable membrane 42 covering the active area of the pH-optode is flexibly attached to a sleeve 43 surrounding the optically transparent carrier element 17, in order to allow for a change in membrane volume. For this purpose the sleeve 43, which is preferably made of a plastics material with memory effect and is shrunk onto the carrier element 17, is provided with a circumferential groove with a fastening element 45 (O-ring).

Figure 5:
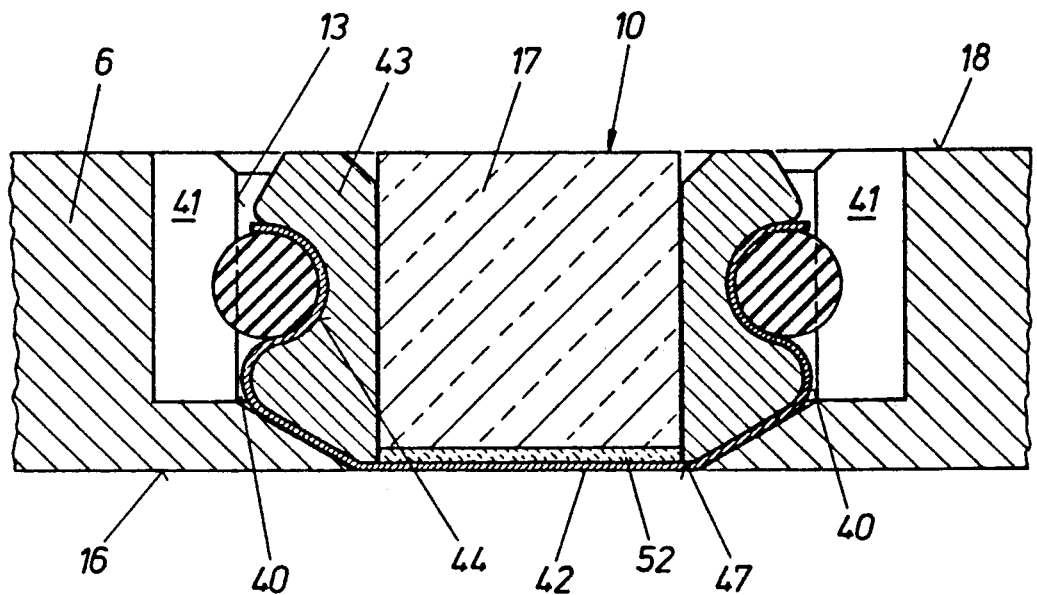

Manufacture of the pH-optode is as follows. From a plastics material with memory effect a sleeve 43 is moulded, the inner diameter of which is smaller by a few tenths of a millimeter than the outer diameter of the optically transparent carrier element 17. The precise configuration of the plastic sleeve 43 with its circumferential groove 44 is shown in FIG. 5 representing a section through the sensor carrier 6 along line V—V in FIG. 4.

In a first step of the manufacturing process the plastic sleeve 43 is held at 100°-110° C. and subsequently widened by means of a metal mandrel to a diameter slightly larger than the outer diameter of the carrier element 17. After this the material is rapidly cooled down to room temperature and the mandrel is removed from the plastic sleeve, which will retain its enlarged dimensions at room temperature.

In the next step the inside of the sleeve 43 is coated with a thin film of a plastics material with a low optical refraction index, such that an optical fiber will be formed in combination with the carrier element with its higher refractive index. The film thickness of the low-refraction plastic cladding should be 10 to 50 micrometers.

In a further step the carrier element of the pH-sensor with its indicator films 52 is placed in the plastic sleeve 43 in such a way that its front face is situated in the same plane as the front end 47 of the sleeve 43. The plastic sleeve 43 together with the pH-optode which is fitted in tightly, is heated to a temperature of 100°-120° C. in a further step. Due to this thermal treatment the plastic 43 starts to shrink on the carrier element 17 along its circumferential groove 44, eventually removing all air or gas bubbles from the space between plastic sleeve 43 and carrier element 17 in the course of the shrinking process.

The $O_2$ optode, for instance, is fabricated in the following way. A mixture of an indicator and a silicone is applied to the center of a carrier element 17, for example a glass cylinder. The glass cylinder with the drop of silicone is positioned underneath a thin, adhesive sheet of black teflon, against which it is pressed to achieve contact. During this process several rows of glass cylinders may be bonded to a sheet simultaneously. The assembly should be allowed to stand for several hours in a shock-proof place, until a homogeneous distribution of the silicone layer on the front surface of the cylinder is obtained. Subsequent polymerization should be performed for at least one hour at 50°-80° C. After the curing phase the teflon sheet together with the sealed-in-place cylinders is put on a punching pad.

A punching tool with a built-in sleeve receiving and guiding the glass cylinder is slipped over the cylinder. By a slight pressure of the punching tool the teflon sheet is cut to the desired diameter.

In order to prepare a $CO_2$ optode suitable glass cylinders are activated by an acid mixture ($HNO_3$ and $H_2SO_4$ at a 1:1 ratio), after which the acid mixture is removed and the cylinders are rinsed with distilled water and dried. The clean and activated cylinders are dried in a drying pistol over phosphorus (V) oxide at temperatures above 100° C. After the drying process the glass cylinders are immersed in dry trichlorovinyl silane and finally rinsed with superpure toluene.

For optical insulation of the $CO_2$ optode a pigmented silicone layer is produced as follows. One component of a two-component silicone rubber is pigmented with ferrous oxide, before the other one is added at the required concentration; this mixture is applied to a teflon layer by a screen-printing technique. Finally, the pigmented silicone layer is polymerized at 50° to 80° C.

A suitable indicator would be hydroxypyrene trisulphonic acid, for example, and a corresponding buffer system should be selected for adjustment of the correct pH value. Suitable additives include polysaccharides and biocides. All of these components are provided in an aqueous phase and are thoroughly mixed with one of the components of a two-component silicone rubber. The sizes of the droplets in the aqueous phase obtained during this process range from 0.1 to 100 micrometers. The indicator solution is intimately mixed with the second component of the silicone rubber and is applied by a screen-printing technique to the pigmented silicone layer prepared as described above. Polymerization should take place at 40° to 80° C.

A very small quantity of a two-component silicone rubber is applied to the acid-activated glass cylinders treated with trichlorovinyl silane, which are then attached to the indicator film of the above sheet (teflon+ pigmented silicone+indicator/silicone). Polymerization should take place for several hours at 20° to 40° C., and then for a minimum of one hour at 50° to 80° C.

Punching of the individual $CO_2$ optodes is essentially the same as described above for the $O_2$ optode.

The individual optodes 10, 11, 12 are sealed into the bores 13, 14, 15 of the sensor carrier 6 by means of a black two-component adhesive.

As is shown for the pH optode 10 in FIG. 5, the optodes are carefully inserted into the corresponding bores 13, 14, 15 and are pressed by means of springs against a resisting element level with the plane 16 of the sensor carrier 6. The pigmented adhesive is filled into the lateral groove-shaped recesses 41 and flows through all gaps to be sealed on account of the capillary forces.

Figure 6:
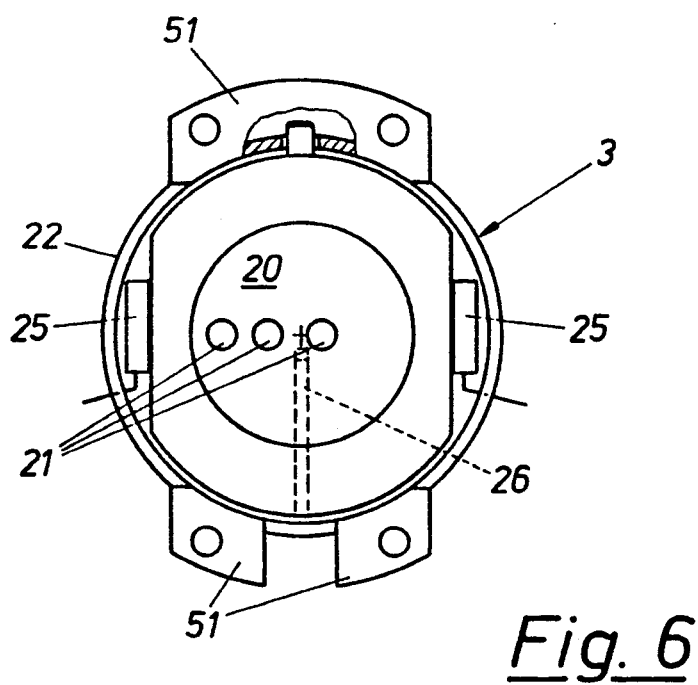

The view from above of the removed optical fiber connector 3 presented in FIG. 6 shows brackets 51 integrated with the side of the housing 22, which are designed for attaching the fiber connector to the supporting frame of the measuring unit. Also shown are the ends 21 of the two-armed waveguides as well as the two heating elements 25 and the thermoelement 26 situated in the middle of the surface-polished plate 20.

Figure 7:
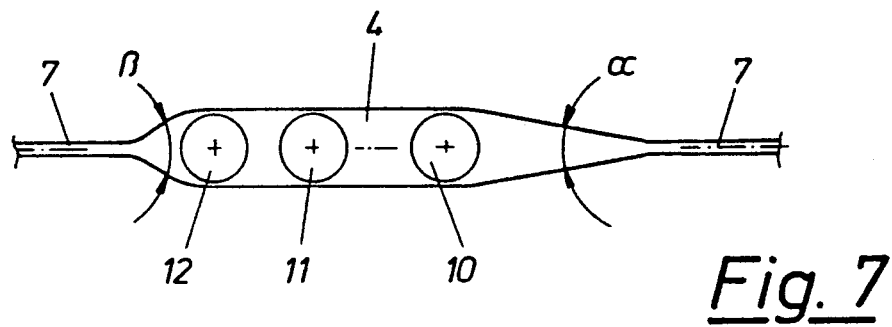
Figure 8:
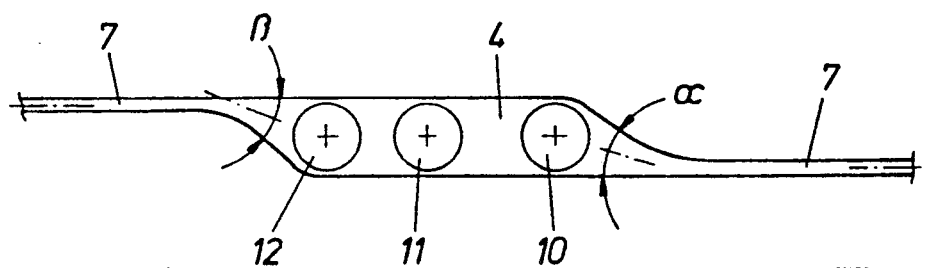
Figure 9:
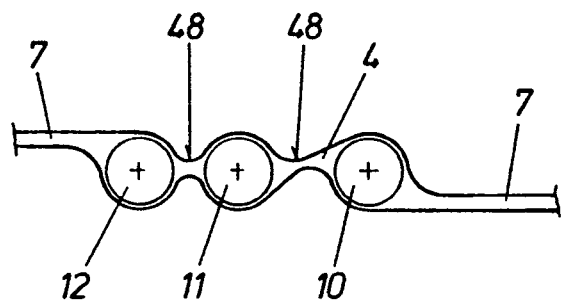

FIGS. 7 to 9 present special shapes of the sample channel 4 configured as a capillary groove.

The symmetrical variant shown in FIG. 7 has an inlet opening angle $\alpha$ of 20° and an outlet opening angle $\beta$ of 60°. Depending on the type of sample medium other angles would be conceivable, ranging from 10° to 60° for the inlet opening angle $\alpha$ and from 10° to 90° for the outlet opening angle $\beta$.

In the variant according to FIG. 8 the flow past the individual optodes 10, 11, 12 is asymmetrical, and in that of FIG. 9 the individual optodes 10, 11, 12 are separated by narrowed passages 48, which will further reduce the measuring volume.

We claim:

1. A device for measuring chemical and physical parameters of a fluid medium, said device comprising:
   a supporting frame which is connectable to an input line for fluid medium and to an output line for fluid medium,
   a measuring unit insertable into said supporting frame to define a sample channel for fluid medium flowing between said input line and said output line, said measuring unit comprising a sensor carrier defining a flat surface facing said sample channel and including a bore therethrough,
   an optode having a indicator film positioned in said bore of said sensor carrier such that said indicator film is positioned in said plane of said sensor carrier and in communication with fluid medium flowing through said sample channel, and
   means for optically exciting said indicator film of said optode and for detecting and evaluating optical signals emitted therefrom so as to measure chemical and physical parameters of said fluid medium.

2. A device according to claim 1, wherein said sensor carrier includes a plurality of bores therethrough; including a plurality of optodes having indicator films which are respectively positioned in said bores of said sensor carrier such that said indicator films are positioned in said plane of said sensor carrier and in communication with fluid medium flowing through said sample channel; and including means for optically exciting each indicator film of each optode and for detecting and evaluating optical signals emitted therefrom.

3. A device according to claim 2, wherein each of said individual optodes is provided with an optically transparent carrier element located in each of said bores of said sensor carrier, which elements end level with a plane of said sensor carrier facing away from said sample channel, and wherein an optical fiber connector is provided which comprises optical connections for each of said optodes, the ends of said optical connections are situated in a surface-polished plate being in contact with said sensor carrier.

4. A device according to claim 1, wherein said supporting frame is furnished with a spring-loaded coupling element in connection with said outgoing sample line, which centers said measuring unit and presses said measuring unit against a coupling element connected with said ingoing sample line, wherein sealing elements being arranged between said coupling elements and capillary bores connected with said sample channel, and wherein said spring-loaded coupling element, having a press lever releasing it.

5. A device according to claim 3, wherein said sensor carrier is configured as a corrosion-resistant metal disk in which said bores for said optodes are placed along the diameter of said metal disk, and wherein said optodes are sealed into said bores by means of an adhesive.

6. A device according to claim 5, wherein said metal disk consists of anodized aluminium and wherein said optodes are pH- and $pO_2$- and $pCO_2$-optodes.

7. A device according to claim 5, wherein a capillary gap is formed between each of said individual optodes and each of said bores in said sensor carrier, and wherein sealant is filled into at least one groove-shaped recess at the periphery of each of said bores extending almost as far as to said plane of said sensor carrier adjacent to said sample channel.

8. A device according to claim 6, wherein said pH-optode is covered by a sleeve containing said optically transparent carrier element and carrying in a circumferential groove a flexible fastening element for a protein-impermeable membrane covering the active area of said pH-optode, and wherein a capillary gap in said sensor carrier situated between said sleeve and said bore is packed with a sealant.

9. A device according to claim 8, wherein said protein-impermeable membrane is made of regenerated cellulose.

10. A device according to claim 8, wherein said sleeve is made of plastics material with memory effect, which is shrunk onto said optically transparent carrier element.

11. A device according to claim 10, wherein the sidewall of said sleeve facing said carrier element is covered with a thin layer whose refractive index is smaller than that of said carrier element.

12. A device according to claim 1, wherein said measuring unit is made of optically transparent material, and wherein an optical waveguide is provided in said supporting frame of said measuring unit for illuminating said sample channel.

13. A device according to claim 3, wherein said fiber connector is provided with a waveguide sleeve contained in a housing, said sleeve contains said optical connections for each of said optodes and has a front end which carries said surface-polished plate being in contact with said sensor carrier and wherein said waveguide sleeve is pressed against said sensor carrier at constant pressure by the force of a spring supported by said housing.

14. A device according to claim 13, wherein said optical fiber connector is provided with at least one heating element and a thermoelement for thermostat control of said sensor carrier in contact with said fiber connector.

15. A device according to claim 2, wherein said sample channel in said measuring unit is configured as a capillary groove extending over each of said indicator films of each of said individual optodes having an inlet opening angle $\alpha$ and an outlet opening angle $\beta$ and wherein capillary bores opening into said sample channel are placed outside of the plane of said capillary groove and are connected to said capillary groove by short bores.

16. A device according to claim 15, wherein said inlet opening angle $\alpha$ in the plane of said capillary groove is 10° to 60°, and the outlet opening angle $\beta$ is 10° to 90°.

17. A device according to claim 16, wherein said inlet opening angle $\alpha$ is 15° to 25° and said outlet opening angle $\beta$ is 30° to 60°.

18. A device according to claim 15, wherein the width of said capillary groove is reduced to narrow passages between said individual optodes.

19. A device according to claim 15, wherein the flow past said individual optodes is asymmetric.

20. A device according to claim 15, wherein said sensor carrier is sealed into said measuring unit by means of a adhesive.

* * * * *